United States Patent [19]

Hurlburt et al.

[11] Patent Number: 4,732,142
[45] Date of Patent: Mar. 22, 1988

[54] DEEP FRICTION MASSAGE ORTHOSIS

[76] Inventors: David Hurlburt, 15 Allen Pl., New Haven, Conn. 06512; Russell Woodman, 3 Tamarac Swamp Rd., Wallingford, Conn. 06492; Barbara M. Steward, 24 Nash St., New Haven, Conn. 06511; R. Kevin Shea, 308 Williams St., Harrison, N.J. 07029

[21] Appl. No.: 926,460

[22] Filed: Nov. 3, 1986

[51] Int. Cl.4 .......................... A61F 5/10; A61F 5/04; A61H 7/00
[52] U.S. Cl. ..................................... 128/77; 128/87 A
[58] Field of Search ................................ 128/77, 87 A

[56] References Cited

U.S. PATENT DOCUMENTS

| D. 234,434 | 3/1975 | Trevino | 273/189 A |
|---|---|---|---|
| 3,217,332 | 11/1965 | Gross | 128/77 |
| 3,235,258 | 2/1966 | Stroburg | 273/189 A |
| 3,328,029 | 6/1967 | Paige | 273/54 B |
| 3,408,077 | 10/1968 | Norwood | 273/54 B |
| 3,467,379 | 9/1969 | Kistner | 273/54 B |
| 3,544,111 | 12/1970 | Crisman et al. | 273/24 |
| 3,595,575 | 7/1971 | Gooch | 273/54 B |
| 3,707,730 | 1/1973 | Slider | 273/54 B |
| 3,728,738 | 4/1973 | Andolino | 273/54 B |
| 3,769,970 | 11/1973 | Swanson | 128/77 |
| 3,788,307 | 1/1974 | Kistner | 128/77 |
| 4,382,439 | 5/1983 | Shen | 128/77 |
| 4,451,044 | 5/1984 | Elliot, Jr. | 273/189 A |
| 4,524,464 | 6/1985 | Primiano et al. | 128/87 A |

FOREIGN PATENT DOCUMENTS 2526654 11/1983 France ................................ 128/77

OTHER PUBLICATIONS

Splints for the Hand, source unknown, however the source at the figures is listed at the bottom of the sheet.

Primary Examiner—Edgar S. Burr
Assistant Examiner—Tonya Lamb
Attorney, Agent, or Firm—M. K. Silverman

[57] ABSTRACT

A deep friction orthosis enhancing the effectiveness of the human hand in the application of deep friction massage therapy. The orthosis includes a partial enclosure having a finger support proportioned to rigidly engage the finger(s); and at least a wrist support integral with the finger(s) support, proportioned to rigidly engage support and direct at least one finger of the hand of the user in a direction having utility in the practice of deep friction massage. The finger support means includes sufficient opening for at least the tip of the supported finger to touch the treated patient's skin.

16 Claims, 13 Drawing Figures

FIG. 3
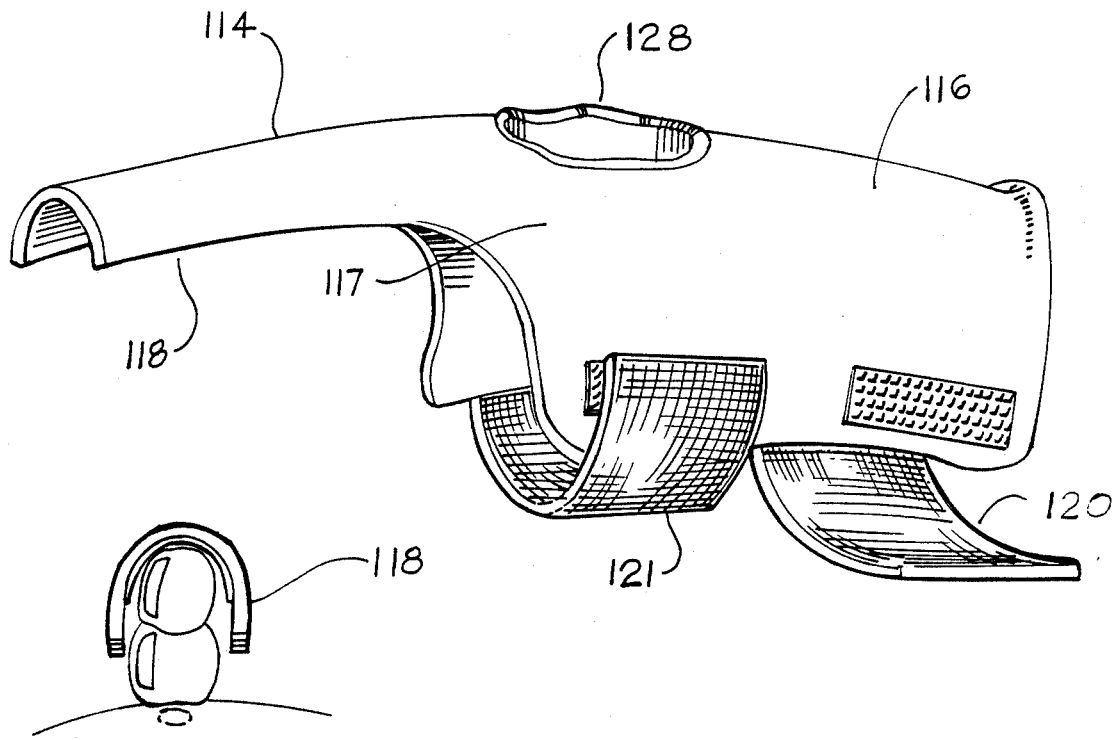
FIG. 4
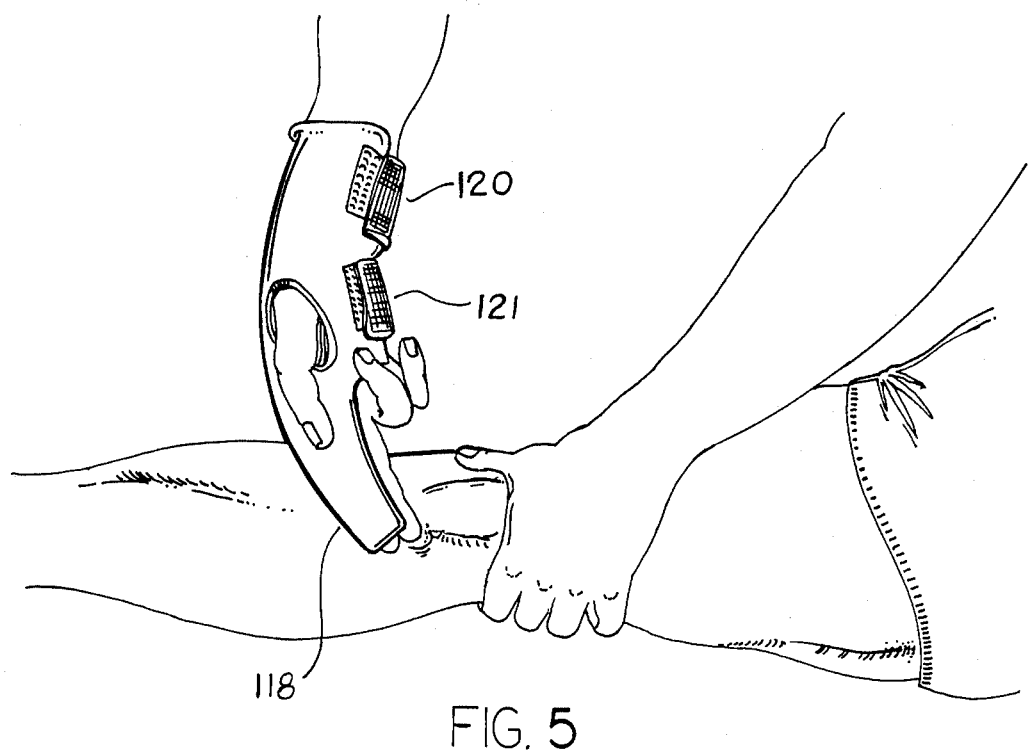
FIG. 5

U.S. Patent  Mar. 22, 1988  Sheet 5 of 5  4,732,142
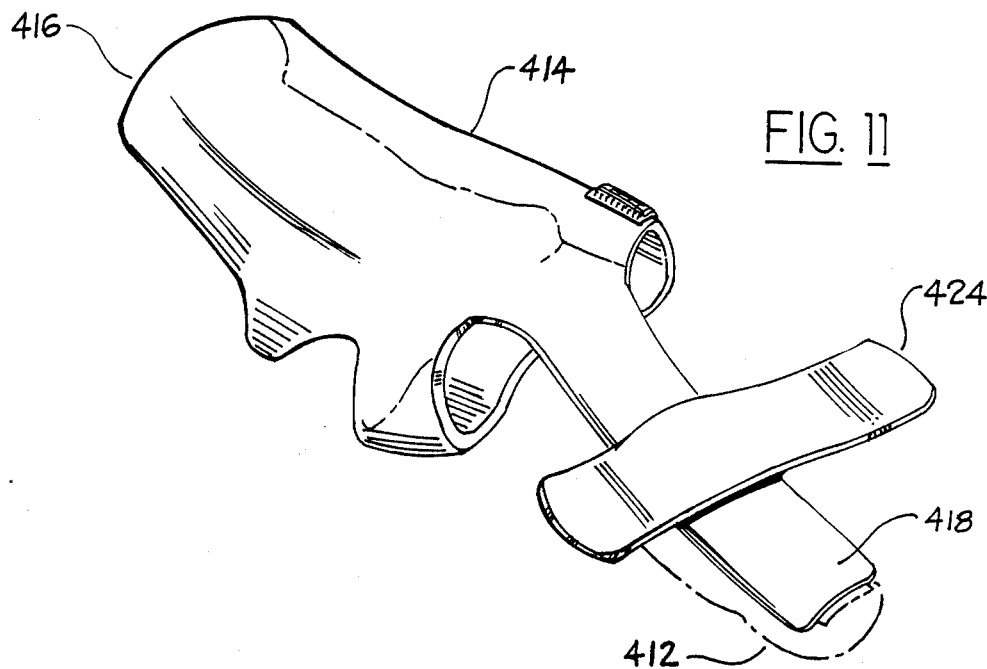
FIG. 11
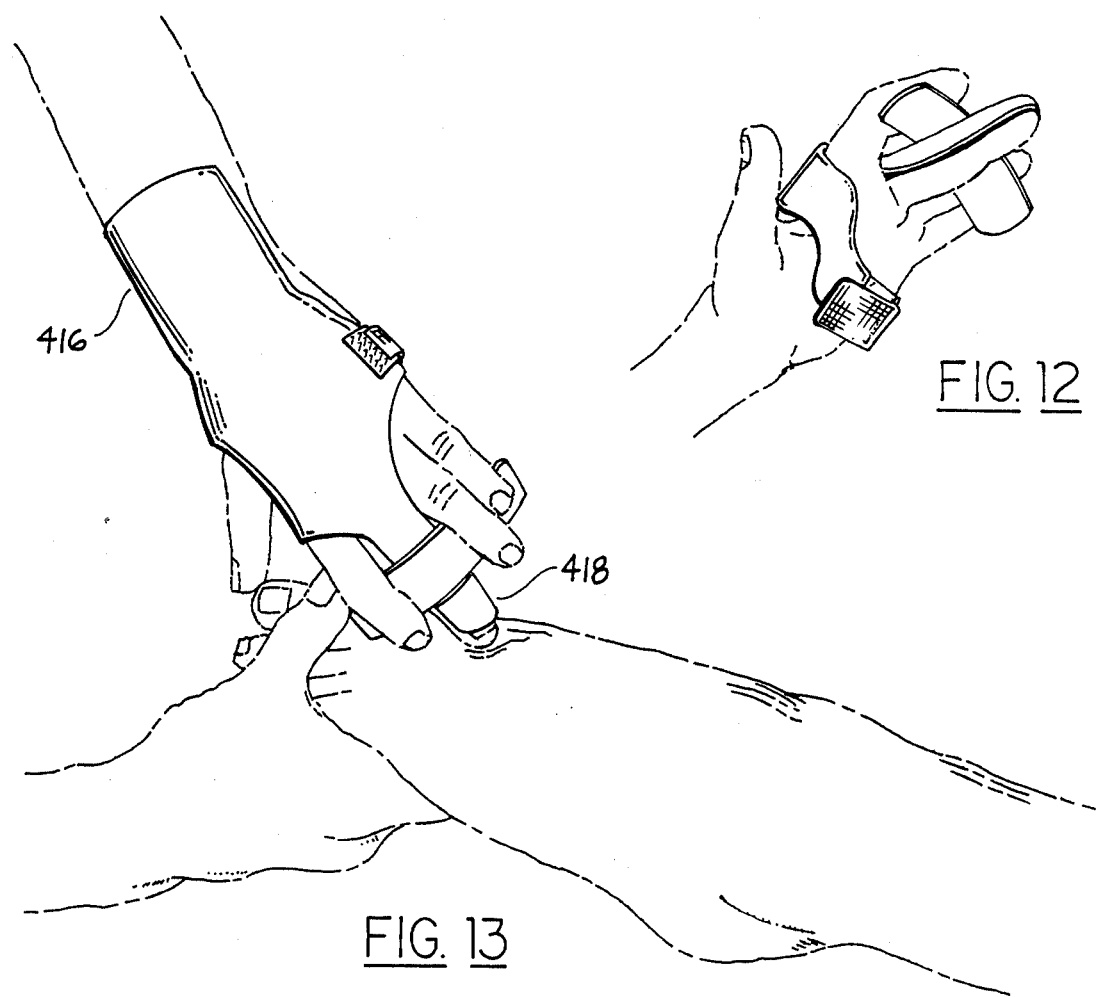
FIG. 12
FIG. 13

DEEP FRICTION MASSAGE ORTHOSIS

BACKGROUND OF THE INVENTION

1. Field of Invention

The present invention relates to the area of implements for use in association with the human hand, such implements being particularly adapted for assisting a physical therapist in the performing of deep friction massage therapy.

2. The Prior Art

The most pertinent prior art known to the inventors are U.S. Pat. Nos. 1,554,510 (1925) to Kirby entitled Massaging Device; 1,885,572 (1932) to Wood entitled Massaging Glove; 4,308,860 (1982) to Sanders entitled Scalp Massaging Implement; and 4,461,285 (1984) to Courtin entitled Manual Massager.

All of the above prior art devices relate to implements adapted for use in connection with the human hand in order to assist the party performing the massage in the execution of a particular type of massage or of the physical communicating of a particular type of sensation to the party receiving the massage, i.e., the patient.

Such prior art devices, while useful in their intended areas, are not relevant to the area of deep friction massage. The area of deep friction massage is of substantial importance in massage therapy and, particularly, in deep friction massage techniques which are most useful in the treatment of certain soft tissue dysfunctions, this particularly includes the ligaments and tendons of the arms, shoulders, legs, and ankles.

A limiting factor in the effectiveness of deep friction massage therapy has been the endurance and strength of the physical therapist. Deep friction massage differs from other types of massage in that it, as its name infers, must penetrate deeply on the skin of the patient such that appropriate contact can be made with the tendons and/or other affected tissue area. Deep friction massage must be preformed for a period of about 20 minutes in a fashion involving continual friction and reciprocation by the fingers of the therapist. The present invention addresses the limitations of strength and endurance of most physical therapist's hands and, thereby, provides a means for providing additional support to the fingers, hand and wrist of the therapist so that a more effective massage therapy can be imparted to the patient.

SUMMARY OF THE INVENTION

The present invention defines a deep friction orthosis for use on the human hand, the device including a single walled partial enclosure comprising finger support proportioned to rigidly engage the finger or fingers of the user with hand and wrist support as an integral part of the total finger(s) support for deep friction massage therapy, said finger support further including sufficient opening to permit at least the tip(s) of the supported finger(s) to touch the patient's skin for deep pressure to the underlying tissues.

It is accordingly an object of the present invention to provide a means for the support of the fingers, hand and wrist of a therapist in order thusly to enhance the strength and endurance of the therapist in the treatment by deep friction massage techniques of his patient.

It is another object to provide a means for more effectively performing deep friction massage.

It is another object to provide a means which will enable the practice of deep friction massage therapy by persons otherwise lacking in sufficient strength to properly perform deep friction massage.

The above and yet further objects and advantages of the present invention will become apparent from the hereinafter set forth Detailed Description of Invention, the Claims, and Drawings appended hereto.

BRIEF DESCRIPTION OF THE DRAWINGS

FIG. 3 is a perspective view of a second embodiment. (Radial Index Finger Splint)

FIG. 4 is an operational view illustrating usage of the second embodiment of the invention.

FIG. 5 is a view taken along the axis of the middle and index finger of a user of the embodiment of FIGS. 3 and 4.

FIGS. 11, 12 and 13 are perspective views of a fifth embodiment of the invention, deep friction massage middle finger splint.

DETAILED DESCRIPTION OF THE INVENTION

A. Deep Friction

The most potent form of massage is deep friction. By this means, massage can reach structures far below the surface of the body. Since the source of pain in patients for whom manual methods are required so often lies in muscle, tendon or ligament, whether as the result of injury or repeated strain, a penetrating technique is clearly essential if such tissues are to be affected. It is thus vital to every physical therapist faced with the treatment of a variety of common disorders that he/she should be fully acquainted with this—the most remedial—type of massage.

When mobility is to be maintained at, or restored to, those moving parts which from their nature or position are apt to develop adhesions or scarring, deep friction is often the method of choice, either alone (as in the case of tendons) or in associa- with passive movements (for some ligamentous lesions) or with active movements without tension on the healing breach (for minor muscular ruptures). An important part of a physical therapist's knowledge consists in choosing and applying whichever type of therapeutic movement is best adapted to the patient's disorder.

The essential fact about deep friction is a follows: it applied therapeutic massage over only a very small area. The massage is the more effective for being so concentrated. Indeed, greater movement may easily be imparted locally by the physical therapist's finger than could ever have been obtained by any amount of the most strenuous exercises and it moves those very tissues on which manipulation has no effect. On account of its purely local action, deep friction must be applied to the exact site of the lesion; otherwise it is useless. Indeed, it is harmful, in so far as it hurts the patient without bringing him any eventual benefit.

Figure 1:
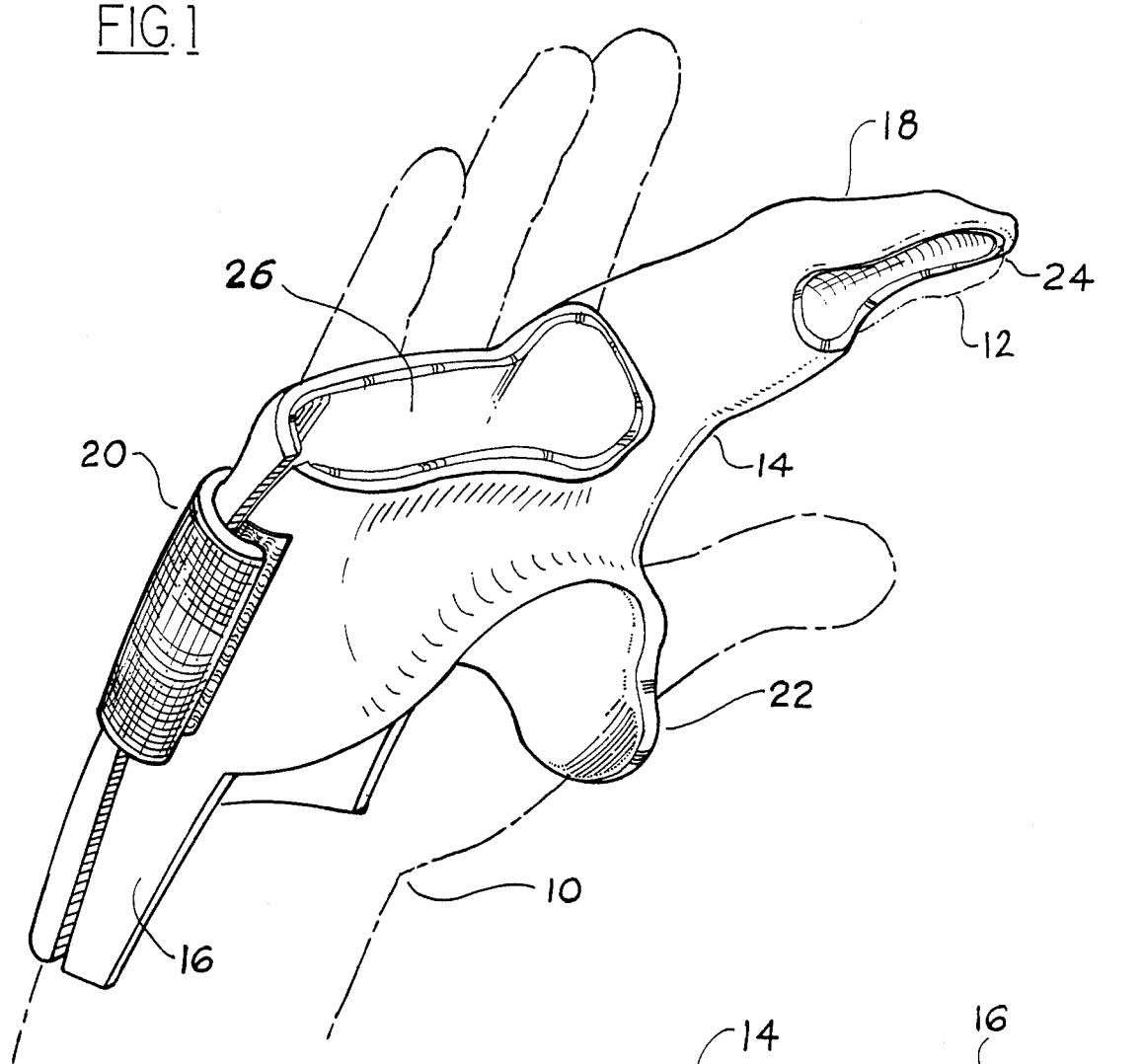
FIG. 1 is a perspective view of a first embodiment of the inventive deep friction orthosis with the hands of a user shown in phantom. (Dorsal Index Finger Splint)
Figure 2:
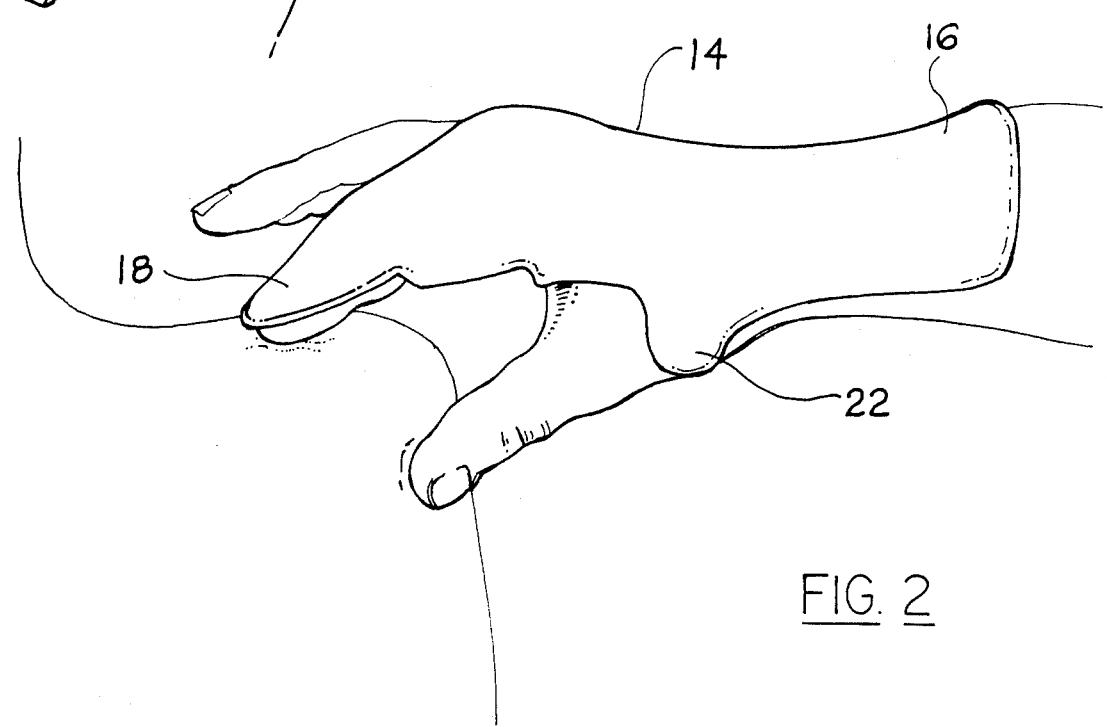
FIG. 2 is an operational view of said first embodiment showing usage of the invention.

With reference to FIGS. 1 and 2, there is shown the present inventive deep friction orthosis adapted for placement over finger 12 and wrist 10 of a user of the orthosis. Therein, it is seen that the orthosis includes a single walled rigid partial enclosure 14 within which the hand of the user may fit. More particularly, the orthosis includes a finger support means 18 which is proportioned to rigidly engage, support and direct one finger of the hand of the user, and is integrally formed with a wrist support means 16 proportioned to rigidly engage the wrist 10 of the user. The three fingers shown at the top of FIG. 1 pass through opening 26.

As is noted in FIG. 1, the finger support means 18 includes a sufficient opening 24 to permit at least the tip of the supported finger 12 of the user to touch the skin of a patient (see FIG. 2).

Shown as element 28 is a concave primer support area.

There is further provided means 20 for selectively changing the degree of skin-to-wall pressure between said partial enclosure 14 and wrist of the user. This pressure adjustment means 20 also comprises means for permitting ease of insertion of the hand of the user into the partial enclosure 14 of the inventive device and thereafter, for the press-fit sealing of means 20 so that the partial enclosure 14, including said finger support means 18 and said wrist support 16, are maintained in suitable close contact with the wrist, hand, and supported finger of the user. It has been found that a male/female velcro material is suitable to assure desired effectiveness of pressure adjustment means 20.

Also shown in FIGS. 1 and 2 is a second, digit support means 22 which, in the embodiment of FIGS. 1 and 2, comprises means for the support of the dorsal metacarpal of the thumb. In other words, in the embodiment of FIGS. 1 and 2, support is provided to both the dorsal side of the index finger and the dorsal metacarpal of the thumb. The resulting deep friction orthosis is of particular value in massaging the supraspinatus tendon of the shoulder as, particularly, is illustrated in FIG. 2. The support provided to the index finger and the thumb makes it possible for the massage therapist to apply greater, deeper, and more precise pressure to the desired soft tissue area. In addition, the endurance of the therapist is greatly enhanced through the use of the inventive finger, hand and wrist support means. This embodiment is particularly useful in the treatment of the supraspinatus tendon.

With reference to the embodiment of FIGS. 3, 4 and 5, there is shown rigid partial enclosure 114 which, in the embodiment of said FIGS. 3 through 5, encompasses finger support 118, palmar support 117, and wrist support 116. The enclosure 114 also includes a thumb opening 128.

Finger support means 118 is adapted to provide radial support to the index finger of the user when the index finger is placed side-by-side with the middle finger such that the middle finger is in pressure contact with the skin of the human body. The use of the embodiment of FIG. 3 is illustrated in FIGS. 4 and 5. This embodiment is particularly useful in the treatment of the achilles tendon and the quadriceps tendon.

The embodiment of FIGS. 3 to 5 also provides for a proximal pressure adjustment means 120 and a distal pressure adjustment means 121. Use of two pressure adjustment means affords superior stability of the deep friction massage device relative to the hand of the massage therapist.

Figure 7:
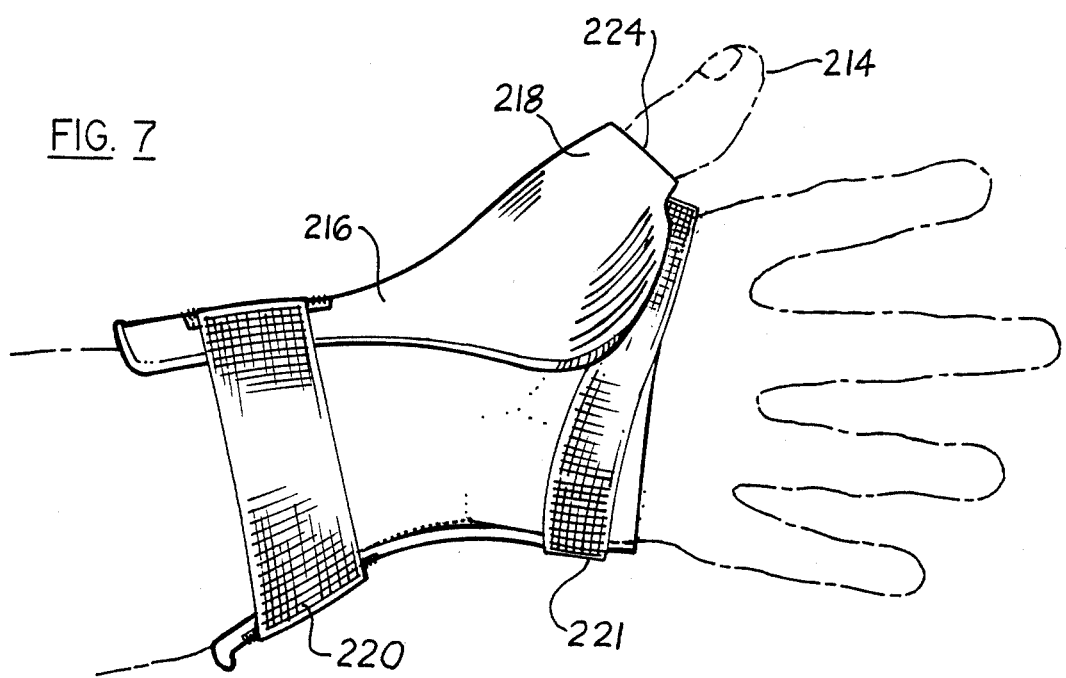
FIG. 7 is a palmar perspective view of the embodiment of FIG. 6.
Figure 6:
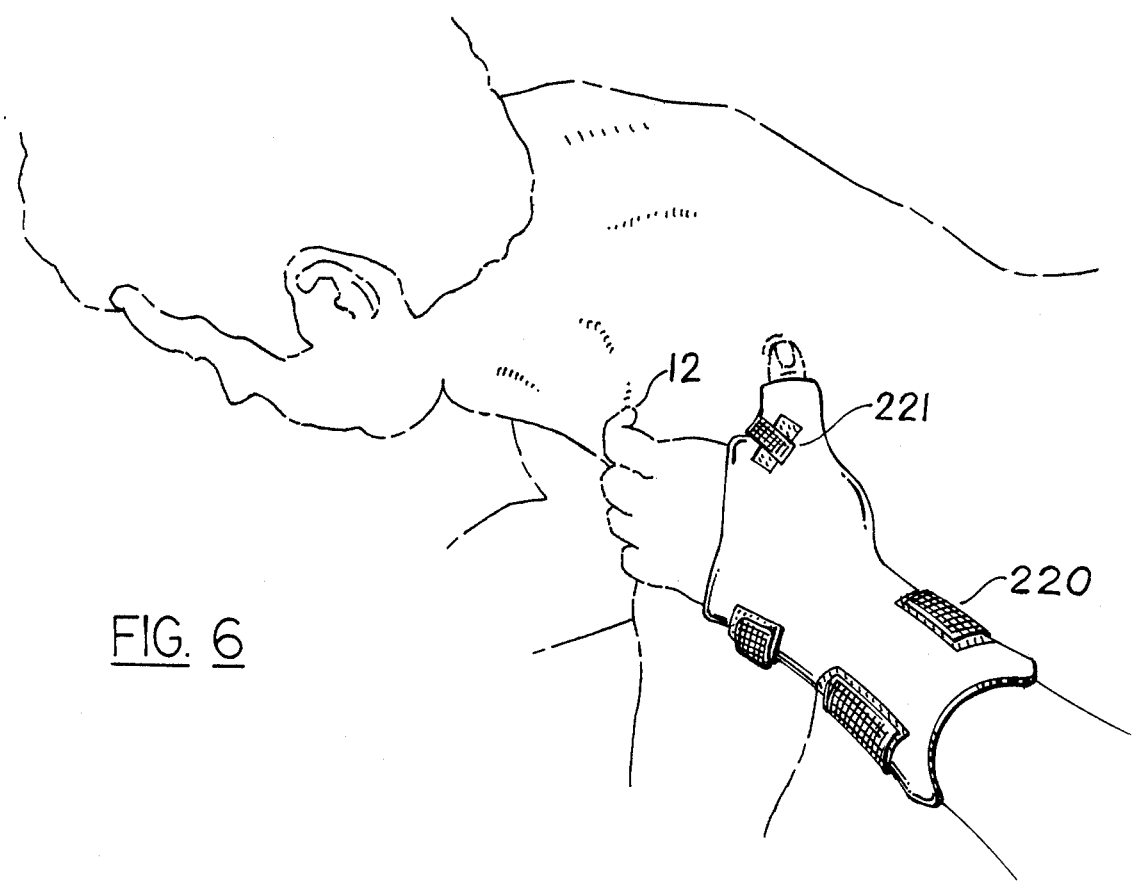
FIG. 6 is an operational view illustrating usage of a third embodiment of the present invention. (Thumb Splint)
Figure 8:
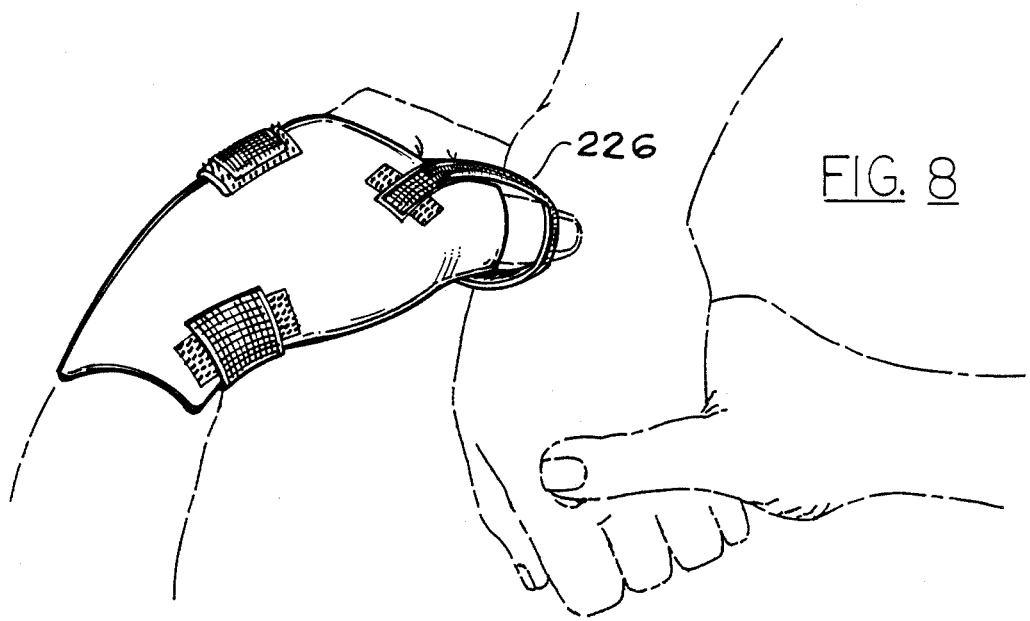
FIG. 8 is an operational view illustrating an additional distal pressure adjustment means of the thumb in the embodiment of FIGS. 6 and 7.

With reference to FIGS. 6 to 8, there is shown a third embodiment of the present inventive deep friction orthosis. Therein is shown finger support 218 which comprises a support for the lower thumb 214 and wrist support 216. The wrist support 216 is held in place through proximal pressure adjustment means 220 and distal pressure adjustment means 221. These pressure adjustment means assure that the wrist will not shift relative to the hand of the user.

As in other embodiments, there is provided a fingertip opening 224 through which the thumb can project and counterbalance point 228. See FIG. 7.

This embodiment is of generalized utility in many forms of massage where the thumb of the physical therapist must be available for use during treatment of the infraspinatus tendon.

In addition, the ligaments of the hand can be specifically massaged with the addition of a thumb pressure adjustment means 226. This assures support, to decrease fatigue of the thumb. See FIG. 8.

Figure 9:
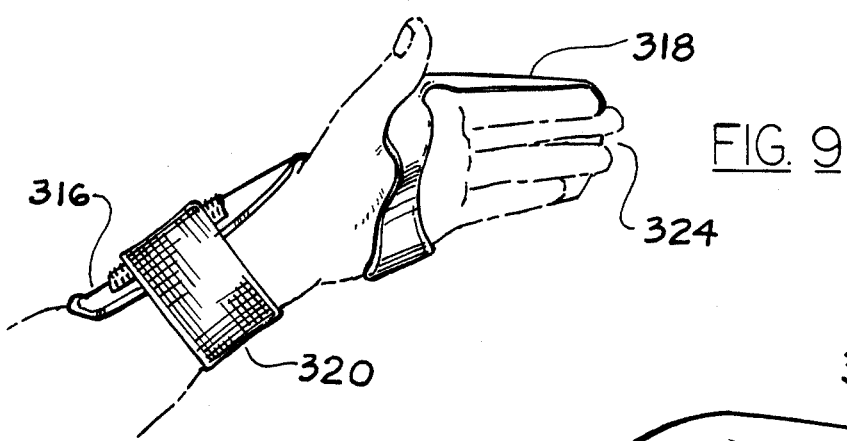
FIG. 9 is a side perspective view of a fourth embodiment of the present invention, with the fingers of the user' shown in phantom. (Dorsal Four Finger Splint)
Figure 10:
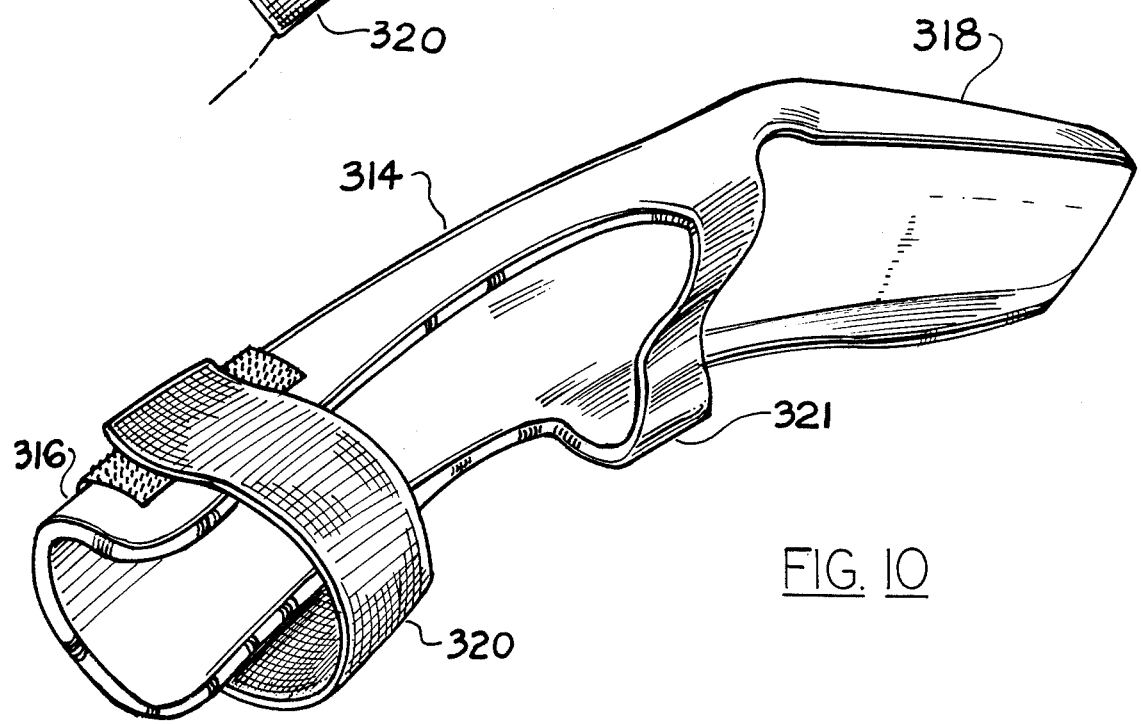
FIG. 10 is a palmar perspective view of the embodiment of FIG. 9.

With reference to FIGS. 9 and 10, there is shown a fourth embodiment, and the preferred embodiment of the present inventive deep friction orthosis. In this embodiment it is seen that the rigid partial enclosure 314 includes a finger support 318 which is adapted to cover all the fingers of the user, excepting the thumb, and a wrist support 316. This embodiment, as in the prior embodiments, provides a finger opening 324 such that the fingers of the therapist are available for massage activity.

Also provided in this embodiment is proximal pressure adjustment means 320 and distal pressure adjustment means 321. These adjustment means insure that the device will not shift relative to the hand of the user during various massage activities. This embodiment is particularly useful in the treatment of the hamstrings and gastrocnemius.

With reference to FIGS. 11 through 13, there is shown a fifth embodiment of the present invention in which a rigid partial enclosure 414 encompasses a middle finger support 418 and a wrist support 416.

The middle finger support 418 includes a fingertip crossbar 424, such that the middle finger is supported on the dorsal side, while the phalanges of the index, ring and little finger are supported on the volar side. With the use of a crossbar 424, the middle finger 412 is stabilized during deep friction massage activity, with reference to FIG. 13, which depicts the dorsal interosseous muscles of the foot.

This embodiment is particularly useful in the treatment of the intrinsics of the hand and foot.

All splint shells are made of high temperature thermoplastic, e.g., polypropelene; within each shell is a layer of pelite, soft cellular foam plastic.

The benefit of these splints to the physical therapist is to relieve fatigue of the therapist's fingers and hand thru the three point support of the splints. This support is to the dorsal and/or radial surface of the finger(s), the palmar surface for the palmar arches, and the dorsal aspect of the wrist for stability.

While various embodiments have been shown and described, it will be understood that the invention may be otherwise embodied, and that within such other embodiments, certain changes in detail and/or the form and arrangement of the parts may be made without departing from the underlying ideas or principles of this invention within the scope of the appended claims.

Having thus described our invention, what we claim as new, useful and non-obvious and, accordingly, secure by Letters Patent of the United States is:

1. A deep friction orthosis having a means to apply three pressure points to the hand of a user giving deep friction massage therapy, said three pressure points consisting of a first pressure point applied proximal to the joint of the wrist of the user on the posterior aspect thereof, a second pressure point applied distal to the joint on the posterior aspect thereof, and a third pressure point applied such that it counterbalances said first and second pressure points, said means to apply comprising a rigid partial enclosure forming a finger support means to rigidly engage, support and direct at least on finger of the user along substantially the entire length of said finger, and including a sufficient opening to permit at least the tip of the supported finger to touch the skin of the patient, said partial enclosure also comprising wrist support means and palmar support means, said finger support means providing said second pressure point, said wrist support means providing said first pressure point, and said palmar support means providing said third pressure point.

2. The orthosis as recited in claim 1 in which said finger support means comprises means for concurrently supporting the middle and index fingers of the user as said fingers are held against each other to permit said middle finger to massage the tissue area of the patient.

3. The orthosis as recited in claim 1 in which said finger support means comprises means for the support of the middle finger.

4. The orthosis as recited in claim 1 in which said finger support means comprises means for the support of the index finger of the user.

5. The orthosis as recited in claim 4 further comprising second finger support means, integrally formed with said partial enclosure, said second finger support means comprising means for the support of dorsal metacarpal of the thumb of the user.

6. The orthosis as recited in claim 5 further comprising:

means for selectively changing the degree of skin-to-wall pressure between said partial enclosure and the finger of the user of the device.

7. The deep friction orthosis as recited in claim 1, further comprising:

means for selectively changing the degree of skin-to-wall pressure between said enclosure and the fingers of a user of the orthosis.

8. The orthosis as recited in claim 7 in which said pressure changing means further comprises means for inserting the wrist into said partial enclosure.

9. The orthosis as recited in claim 8 in which said finger support means comprises means for the support of the index finger of the user.

10. The orthosis as recited in claim 8 in which said finger support means comprises means for support of the lower thumb.

11. The orthosis as recited in claim 8 in which said finger support means comprises means for concurrently supporting the dorsal side of all fingers of the user except the thumb.

12. The orthosis as recited in claim 8 in which said finger support means comprises means for the support of the middle finger.

13. The orthosis as recited in claim 8 in which said pressure changing means comprises male/female VELCRO-like elements.

14. The orthosis as recited in claim 8 in which the said finger support means comprises means for dorsal support of the middle finger with a crossbar for volar support of index, ring and little finger.

15. The orthosis as recited in claim 8 in which said finger support means comprises means for concurrently supporting the middle and index fingers of the user as said fingers are held against each other to permit said middle finger to massage the tissue area of the patient.

16. The orthosis as recited in claim 15 in which said wrist support means includes an opening permitting the thumb of the user to pass through the walls of said partial enclosure.

* * * * *